(12) United States Patent
Ippoliti et al.

(10) Patent No.: US 8,187,623 B2
(45) Date of Patent: May 29, 2012

(54) MEDICAL COPOLYMERS

(75) Inventors: J. Thomas Ippoliti, St. Paul, MN (US); Scott Schewe, Eden Prairie, MN (US); Robert W. Warner, Woodbury, MN (US); Michele Zoromski, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 345 days.

(21) Appl. No.: 12/491,467

(22) Filed: Jun. 25, 2009

(65) Prior Publication Data

US 2009/0324679 A1 Dec. 31, 2009

Related U.S. Application Data

(60) Provisional application No. 61/075,416, filed on Jun. 25, 2008.

(51) Int. Cl.
*A61F 2/00* (2006.01)
*A61K 9/14* (2006.01)

(52) U.S. Cl. ........................ 424/423; 424/486
(58) Field of Classification Search .................. 424/423, 424/486
See application file for complete search history.

(56) References Cited

U.S. PATENT DOCUMENTS

| | | |
|---|---|---|
| 2006/0147490 A1 | 7/2006 | Bowden et al. |
| 2007/0141104 A1 | 6/2007 | Hauenstein |
| 2007/0269480 A1 | 11/2007 | Richard et al. |
| 2008/0142454 A1 | 6/2008 | Emrick et al. |

FOREIGN PATENT DOCUMENTS

| | | |
|---|---|---|
| JP | 2004250613 A | 9/2004 |
| WO | 98/55487 A1 | 12/1998 |
| WO | 01/01957 A1 | 1/2001 |
| WO | 02/055121 A1 | 7/2002 |

OTHER PUBLICATIONS

R. Virmani et al.,"Localized Hypersensitivity and Late Coronary Thrombosis Secondary to a Sirolimus-Eluting Stent", Circulation Feb. 17, 2004, 109(6) 701-5.
S. Ranade et al., "Physical characterization of controlled release of paclitaxel from the TAXUS™ Express2™ drug-eluting stent", Journal of Biomedical Materials Research Part A, 71A (2004) 625-634.
A.L. Lewis et al., "Blending in with the Body", J. Chem. Ed., 79(3), Mar. 2002, 321-326.
R. Collingwood et al., "Stent-Based Delivery of ABT-578 via a Phosphorylcholine Surface Coating Reduces Neointimal Formation in the Porcine Coronary Model", Catheter Cardiovasc. Interv., 65 (2005) 227-232.
N. Malik et al., "Phosporylcholine-Coated Stents in Porcine Coronary Arteries: In Vivo Assessment of Biocompatibility", J. Invasive Cardiol. 13 (2001) 193-201.
J. A. Hayward et al., "Biomembrane Surfaces as Models for Polymer Design: The Potential for Haemocompatibility", Biomaterials 5 (1984) 135.
Tegoulia et. al., "Surface Properties, Fibrinogen Adsorption, and Cellular Interactions of a Novel Phosphorylcholine-Containing Self-Assembled Monolayer on Gold", Langmuir 2001, 17, 4396-4404.
D.M. Whelan et al., "Biocompatibility of phosphorylcholine coated stents in normal porcine coronary arteries", Heart ;83 (2000) 338-345.
J. Das et al., "Synthesis and Pharmacological Evaluation of 5, 6exo -Epoxy-7-oxabicyclo[ 2.2.1] heptane Derivatives", J. Med. Chem. 31 (1988) 930-935.
S. Chen et al., "Strong Resistance of Oligo(phosphorylcholine) Self-Assembled Monolayers to Protein Adsorption", Langmuir 2006, 22, 2418-2421.
A. L. Lewis et al., "Synthesis and Characterization of phosphorylcholine-based polymers useful for coating blood filtration devices", Biomaterials 21 (2000) 1847-1859.
S.F. Zhang et al., "Physical and Biological Properties of Compound Membranes Incorporating a Copolymer with a Phosphoylcholine Head Group", Biomaterials 19 (1998) 691-700.
Ring Opening Metathesis Polymerization, 4 pp., downloaded from http://www.ilpi.com/organomet/romp.html on Mar. 10, 2008.
T. M. Sisson et al., "Novel polymer architectures via the selective polymerization of lyotropic liquid crystals of heterobifunctional amphiphiles", J. Am. Chem. Soc. 1998, 120, 2322-2329.
V. Amir-Ebrahimi et al., "Copolymerization of cycloalkenes as a probe of the propagation steps in olefin metathesis", Journal of Molecular Catalysis A: Chemical 115 (1997) 85-94.

*Primary Examiner* — Gina C Yu
*Assistant Examiner* — Michael B Pallay
(74) *Attorney, Agent, or Firm* — Mayer & Williams PC; David B. Bonham; Keum J. Park (57) ABSTRACT

Medical copolymers are provided which comprise (a) a polymer backbone comprising (i) a plurality of —C=C— groups within the polymer backbone, (ii) a plurality of —$R_9$— groups within the polymer backbone, wherein $R_9$ comprises a radical-substituted C2-C10 cyclic or heterocyclic group, or (iii) both a plurality of —C=C— groups and a plurality of —$R_9$— groups within the polymer backbone, (b) a plurality of hydrocarbon-based pendant groups along the polymer backbone that comprise a saturated or unsaturated carbon chain of at least four carbons in length, and (c) a plurality of zwitterionic pendant groups along the polymer backbone that comprise a positively charged quaternary ammonium group and a negatively charged phosphate group. Methods of forming such copolymers, medical products that contain such copolymers, and methods of making such medical products are also disclosed.

17 Claims, 5 Drawing Sheets

Fig. 6

MEDICAL COPOLYMERS

RELATED APPLICATIONS

This application claims priority from U.S. provisional application 61/075,416, filed Jun. 25, 2008, which is incorporated by reference herein in its entirety.

FIELD OF THE INVENTION

The present invention relates generally to medical copolymers, including methods of making medical copolymers and medical products that employ medical copolymers.

BACKGROUND OF THE INVENTION

Copolymers are an important class of polymers and have numerous commercial applications. For instance, their unique properties, whether in pure form, in blends, in melts, in solutions, in dispersions, and so forth, lead to their use in a wide range of medical products.

As a specific example, numerous copolymer-based medical articles have been developed for implantation or insertion into the body. For instance, various state of the art medical devices consist of a medical device substrate with a copolymer-containing coating that serves as a reservoir for one or more therapeutic agents. Specific examples include drug eluting coronary stents, commercially available from Boston Scientific Corp. (TAXUS), Johnson & Johnson (CYPHER) and others, which have become the standard of care for maintaining vessel patency after balloon angioplasty. These products are based on metallic expandable stents with copolymer-containing coatings that release antirestenotic drugs in a profile effective to inhibit the smooth muscle proliferation that is associated with restenosis (vessel reclosure). CYPHER stents are coated with a layer of a blend of ethylene-vinyl acetate copolymer and poly(n-butyl methacrylate) and contain sirolimus as an anti-restenotic agent. R. Virmani et al., *Circulation* 2004 Feb. 17, 109(6) 701-5. The polymer carrier technology in the TAXUS drug-eluting stent consists of a thermoplastic elastomer poly(styrene-b-isobutylene-b-styrene) (SIBS) with microphase-separated morphology resulting in optimal properties for a drug-delivery stent coating. S. Ranade et al., "Physical characterization of controlled release of paclitaxel from the TAXUS™ Express2™ drug-eluting stent," *Journal of Biomedical Materials Research Part A*, 71A (2004) 625-634.

Another example of a medical copolymer is a synthetic phosphorylcholine copolymer, specifically, a copolymer of 2-methacryloyloxyethyl phosphorylcholine and lauryl methacrylate, which has been proposed for use in medical devices. See, e.g., A. L. Lewis et al., *J. Chem. Ed.*, 79(3), March 2002, 321-326.

There is a continuing need for novel copolymers, which can be used in medical products, including pharmaceutical compositions and medical articles such as implantable and insertable medical devices, among others.

SUMMARY OF THE INVENTION

According to an aspect of the present invention, medical copolymers are provided which comprise (a) a polymer backbone comprising (i) a plurality of —C═C— groups within the polymer backbone, (ii) a plurality of —$R_9$— groups within the polymer backbone, wherein $R_9$ comprises a radical-substituted C2-C10 cyclic or heterocyclic group, or (iii) both a plurality of —C═C— groups and a plurality of —$R_9$— groups within the polymer backbone, (b) a plurality of hydrocarbon-based pendant groups along the polymer backbone that comprise a saturated or unsaturated carbon chain of at least four carbons in length, and (c) a plurality of zwitterionic pendant groups along the polymer backbone that comprise a positively charged quaternary ammonium group (i.e., $R_4N^+$, where $R_4$ is an organic radical) and a negatively charged phosphate group.

Further aspects of the invention, among others, relate to methods of forming such copolymers, medical products that contain such copolymers, and methods of making such medical products.

A variety of physical and chemical characteristics may be provided by the copolymers of the invention, including one or more of the following, among others: enhanced biocompatibility, anti-thrombogenicity, resistance to non-specific protein adsorption and tailorable hydrophobic/hydrophilic character (influencing, for example, wettability, as well as water diffusivity and therapeutic agent diffusivity).

These and other aspects, embodiments and advantages of the present invention will become immediately apparent to those of ordinary skill in the art upon review of the Detailed Description and Claims to follow.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

According to an aspect of the present invention, medical copolymers are provided which comprise (a) a polymer backbone comprising (i) a plurality of —C═C— groups within the polymer backbone, (ii) a plurality of —$R_9$— groups within the polymer backbone, wherein $R_9$ comprises a radical-substituted C2-C10 cyclic or heterocyclic group, or (iii) both a plurality of —C═C— groups and a plurality of —$R_9$— groups within the polymer backbone, (b) a plurality of hydrocarbon-based pendant groups along the polymer backbone that comprise a saturated or unsaturated carbon chain of at least four carbons in length, and (c) a plurality of zwitterionic pendant groups along the polymer backbone that comprise a positively charged quaternary ammonium group (i.e., $R_4N^+$, where $R_4$ is an organic radical) and a negatively charged phosphate group. In certain embodiments, the polymer backbone will comprises a plurality of —$R_9$—C=C— groups with the polymer backbone.

As used herein, "polymers" are molecules containing multiple copies (e.g., from 5 to 10 to 25 to 50 to 100 to 250 to 500 to 1000 or more copies) of one or more constitutional units, commonly referred to as monomers. As used herein, "monomers" may refer to free monomers and to those are incorporated into polymers, with the distinction being clear from the context in which the term is used.

Polymers may take on a number of configurations, which may be selected, for example, from cyclic, linear and branched configurations, among others. Branched configurations include star-shaped configurations (e.g., configurations in which three or more chains emanate from a single branch point), comb configurations (e.g., configurations having a polymer backbone and a plurality of side chains, also referred to as "graft" configurations), dendritic configurations (e.g., arborescent and hyperbranched polymers), networked (e.g., crosslinked) configurations and so forth.

As used herein, "homopolymers" are polymers that contain multiple copies of a single constitutional unit. As used herein, "copolymers" are polymers that contain multiple copies of at least two dissimilar constitutional units, examples of which include random, statistical, gradient, periodic (e.g., alternating) and block copolymers.

As previously indicated, according to one aspect of the present invention, medical copolymers are provided which comprise (a) a polymer backbone comprising a plurality of —C=C— groups, a plurality of —$R_9$— groups, or both within the polymer backbone, where $R_9$ is defined above, (b) a plurality of hydrocarbon-based pendant groups that comprise a saturated or unsaturated carbon chain of at least four carbons in length, and (c) a plurality of zwitterionic pendant groups that comprise a positively charged quaternary ammonium group and a negatively charged phosphate group.

In some embodiments, the medical copolymers of the invention comprise a polymer backbone that comprises (i) a plurality of —C=C— groups within the polymer backbone, (ii) a plurality of —$R_9$— groups within the polymer backbone, or (iii) both a plurality of —C=C— groups and a plurality of —$R_9$— groups within the polymer backbone. For example, the —$R_9$— may comprise a radical-substituted C4-C10 cyclic group or a radical-substituted C3-C10 heterocyclic group in certain embodiments.

In certain embodiments, the medical copolymers of the invention comprise a polymer backbone that comprises a plurality —$R_9$—C=C— groups and/or a plurality of —$R_9$—C—C— groups within the polymer backbone.

In certain embodiments, the medical copolymers of the invention comprise a polymer backbone that comprises a plurality of the following groups within the polymer backbone:

(i.e., —$R_9$—C=C—, where —$R_9$— is radical-substituted C5 cyclic alkyl group), (i.e., —$R_9$—C=C—, where —$R_9$— is radical-substituted C5 cyclic alkenyl group), and (i.e., —$R_9$—C=C—, where —$R_9$— is radical-substituted C4 heterocyclic alkyl group), where n is an integer and $R^1$ and $R^2$ are organic radicals which may be the same or different from one another. Various $R^1$ and $R^2$ radicals are described below.

In certain additional embodiments, the medical copolymers of the invention comprise a polymer backbone that comprises a plurality of the following groups within the polymer backbone:

(i.e., —$R_9$—C—C—, where —$R_9$— is radical-substituted C5 cyclic alkyl group) or (i.e., —$R_9$—C—C—, where —$R_9$— is radical-substituted C4 heterocyclic alkyl group).

Medical copolymers in accordance with the invention may be formed via ring-opening metathesis polymerization (ROMP), which uses strained cyclic olefins and a metathesis catalyst to produce homopolymers and copolymers. A few specific examples of monomers with substantial ring strain include norbornene, and its derivatives, for example,

(a radical substituted 7-oxanorbornene derivative).

In various aspects, copolymers in accordance with the invention are designed to be mimics of dipalmitoylphosphatidyl choline (DPPC),
i.e., where n is 14. For example, in some embodiments, the medical copolymers of the invention contain zwitterionic groups that mimic the phosphoryl choline head-group of DPPC. Moreover, in some embodiments, the medical copolymers of the invention contain hydrocarbon-based pendant groups that mimic the hydrophobic palmitoyl tail-groups of DPPC.

Found in abundance within the cell wall membrane of red blood cells, DPPC is considered to be a factor in the non-thrombogenic character of these cells. R. Collingwood et al., Catheter Cardiovasc. Interv., 65 (2005) 227-232. In animal models, a coating of phosphoryl choline, has been shown to reduce thrombus formation on metallic stents. N. Malik et al., J. Invasive Cardiol. 13 (2001) 193-201. In the 1980's, Chapman et al. showed that the outer (extracellular) side of red blood cells is composed primarily of DPPC. James A. Hayward and D. Chapman, Biomaterials 5 (1984) 135. Chapman and others have shown that the phosphoryl choline head-group of DPPC is a key to conferring biocompatibility to the cell wall. Without wishing to be bound by theory, current research favors the mechanism that the highly hydrophilic phosphoryl choline head-group of DPPC binds a large number of water molecules around the head-group. When a protein approaches the cell surface, it encounters a large hydration sphere associated with the phosphoryl choline head-groups of the DPPC in the cell wall and, without any formal charge to initiate further interaction, the protein desorbs from the surface without a change in conformation. A. L. Lewis et al., J. Chem. Ed., 79(3), March 2002, 321-326.

As previously indicated, copolymers in accordance with the invention comprise hydrocarbon-based pendant groups that comprise a saturated or unsaturated carbon chain of at least four carbons in length. Examples of such hydrocarbon-based pendant groups include, for example, pendant groups selected from $-(CH_2)_p-CH_3$, $-(CH_2)_m-O-(CH_2)_p-CH_3$, $-(CH_2)_m-CO-O-(CH_2)_p-CH_3$, and $-(CH_2)_m-O-CO-(CH_2)_p-CH_3$, among others, where m is an integer between 0 and 5 (i.e., 0, 1, 2, 3, 4 or 5), and p is an integer between 4 and 25 (i.e., 4, 5, 6, 7, 8, 9, 10, 11, 12, 13, 14, 15, 16, 17, 18, 19, 20, 21, 22, 23, 24 or 25). In some embodiments, at least one of the carbon-carbon single bonds ($-CH_2-CH_2-$) in the saturated $-(CH_2)_n-$ portion of the hydrocarbon-based groups may be replaced by a carbon-carbon double bond ($-CH=CH-$).

In specific embodiments, polymers in accordance with the invention may comprise incorporated monomers such as and saturated versions of the same, i.e., wherein $R^1$, $R^2$, or both, may be selected from the hydrocarbon-based pendant groups described above, among other radicals. In some embodiments, one of $R^1$ and $R^2$ may be selected from $-H$, $-(CH_2)_m-OH$, $-(CH_2)_m-COOH$, $-(CH_2)_m-X$ and $-(CH_2)_m-NH_2$, where X is a halogen and m is an integer between 0 and 5.

As previously indicated, copolymers in accordance with the invention comprise zwitterionic pendant groups that comprise a positively charged quaternary ammonium group and a negatively charged phosphate group. For example, in some embodiments, the copolymers comprise zwitterionic groups selected from groups, where k and m are independently integers between 0 and 5 (i.e., 0, 1, 2, 3, 4 or 5).

In certain embodiments, polymers in accordance with the invention may comprise incorporated monomers such as and saturated forms of the same, i.e., wherein $R^3$, $R^4$, or both, may be selected from the preceding zwitterionic pendant groups. In some embodiments, one of $R^3$ and $R^4$ is selected from —H, —$(CH_2)_m$—OH, —$(CH_2)_m$—COOH, —$(CH_2)_m$—X and —$(CH_2)_m$—$NH_2$, where X is a halogen and m is an integer between 0 and 5.

The number of methylene groups, —$(CH_2)$—, in the preceding hydrocarbon-based and zwitterionic pendant groups may be varied to change the hydrophilic/hydrophobic balance of the copolymers of the invention. For example, one may wish to closely match the overall hydrophilic/hydrophobic balance of the copolymer to that of DPPC. In certain embodiments, the molar ratio between the hydrocarbon-based groups and the zwitterionic groups may be approximately two to one to mimic the ratio of these species in DPPC.

Moreover, because methylene groups are hydrophobic, increasing the number of methylene groups decreases the solubility of the copolymer in aqueous liquids (e.g., body fluids) and may therefore improve the in vivo stability of the copolymer. In addition, changing the hydrophilic/hydrophobic balance of the copolymers of the invention may also be used to modify the release characteristics of any therapeutic agent that may be disposed within or beneath polymeric regions (e.g., layers) that contain the copolymers.

As previously noted, polymers in accordance with the invention may be formed via the ROMP process, which uses strained cyclic olefins and a metathesis catalyst (e.g., a second generation Grubbs catalyst, for example, a ruthenium carbine catalyst) to produce homopolymers and copolymers. In the ROMP process, the monomer is a strained cyclic olefin, such that a driving force for the ROMP reaction is the relief of ring strain. Polymers produced in the ROMP reaction typically have a very narrow range of molecular weights, with polydispersities (i.e., the weight average molecular weight divided by the number average molecular weight) that are commonly in the range of 1.03 to 1.10, among other possibilities. ROMP systems are typically living-type polymerization systems, allowing sequential monomer addition and thus the formation of block copolymers (e.g., diblock copolymers, triblock copolymers, etc.) by this technique.

Figure 1:
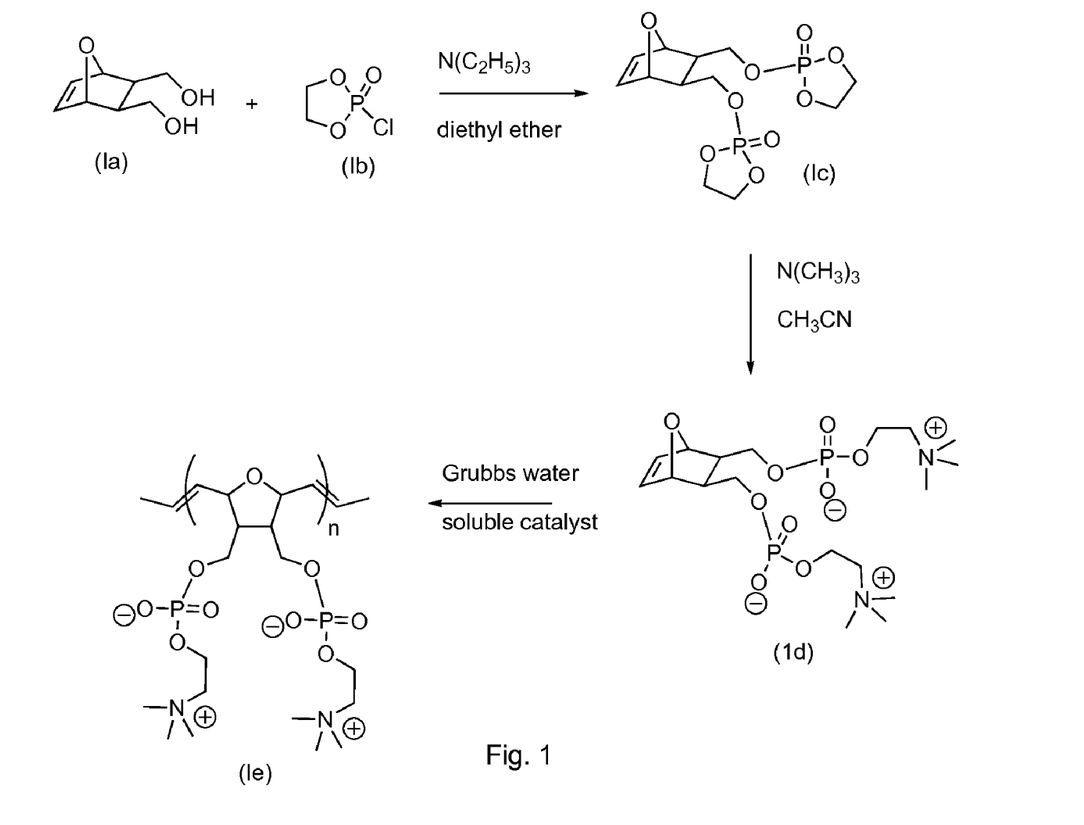
FIG. 1 is a schematic illustration of a method of forming monomers and polymers with zwitterionic groups, in accordance with an embodiment of the invention.

In one specific example, a reaction scheme as illustrated in FIG. 1 may be employed, whereby 2,3-dihydroxymethyl 7-oxanorbornene (Ia) and 2-chloro-1,3,2-dioxaphospholane (Ib) are reacted in a solution containing triethylamine in diethyl ether to produce 2,3-diphosphorylmethyl 7-oxanorbornene (Ic). This species is then reacted in a solution of trimethylamine in acetonitrile to form the diphosphorylcholine norbornene compound (Id). See, e.g., Cooper et. al., Langmuir 2001, 17, 4396. This monomer may then be used in a ROMP reaction to form a polymer (Ie), where n is an integer.

Figure 2A:
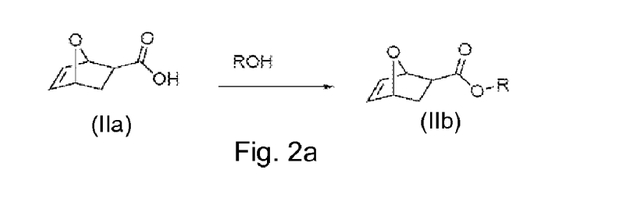
FIG. 2a is a schematic illustration of a method of forming monomers with hydrocarbon based groups, in accordance with an embodiment of the invention.
Figure 2B:
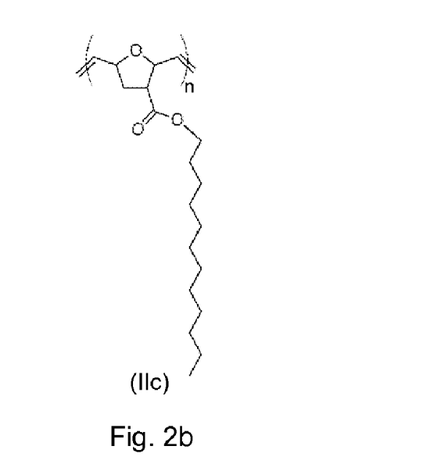
FIG. 2b is a schematic illustration of poly(2-carboxyl,7-oxanorbornene, dodecyl ester).

With respect to hydrocarbon-based monomers, FIG. 2a shows a process whereby a 2-carboxyl, 3-carboxyl, or 2,3-carboxyl norbornene derivative, in particular, 2-carboxyl,7-oxanorbornene (IIa), may be provided with one or more hydrocarbon-based groups via an esterification reaction with a hydroxyl terminated compound ROH, where R is an organic radical, for example, where R is —$(CH_2)_p$—$CH_3$, —$(CH_2)_m$—O—$(CH_2)_p$—$CH_3$, —$(CH_2)_m$—CO—O—$(CH_2)_p$—$CH_3$ or —$(CH_2)_m$—O—CO—$(CH_2)_p$—$CH_3$, wherein m is an integer between 0 and 5 and p is an integer between 4 and 25. The resulting monomer (IIb) may then be used in a ROMP process to form a polymer block with hydrocarbon pendant groups. For example, poly(2-carboxyl,7-oxanorbornene, dodecyl ester) (IIc) may be formed as shown in FIG. 2b, where n is an integer.

Zwitterionic and hydrocarbon-based monomers such as those described above may be polymerized sequentially using a monofunctional initiator to form an AB type block copolymer, wherein the zwitterionic monomer block is designated "A" and the hydrocarbon-based monomer block is designated "B". As another example, polymers comprising hydrocarbon-based monomers may be joined to polymers comprising zwitterionic polymers by a suitable linking chemistry, for example, to form AB type, ABA type or BAB type block copolymers.

Note that the hydrocarbon-based monomers groups are relatively hydrophobic while the zwitterionic pendant groups are relatively hydrophilic. Thus, where an AB block copolymer is formed with a first polymer block containing hydrocarbon-based pendant groups and a second polymer block containing zwitterionic pendant groups, the resulting polymer will be amphiphilic. Amphiphilic polymers may be useful in the formation of micelles (e.g., for the administration of a water insoluble drug), among other uses.

In other embodiments, copolymers in accordance with the invention may be formed using precursor polymers, in which pendant groups of the precursor polymers are modified to create zwitterionic pendant groups or hydrocarbon-based pendant groups such as those described above. Examples of precursor polymers include, for example, those containing the following monomers:

among others, where $R^5$, $R^6$, or both, may be selected from —$(CH_2)_m$—OH, —$(CH_2)_m$—COOH, —$(CH_2)_m$—X and —$(CH_2)_m$—$NH_2$, where X is a halogen (e.g., Cl, I, etc.) and where m ranges from 0 to 5. In some embodiments, one of $R^5$ and $R^6$ may be —H.

Figure 3:
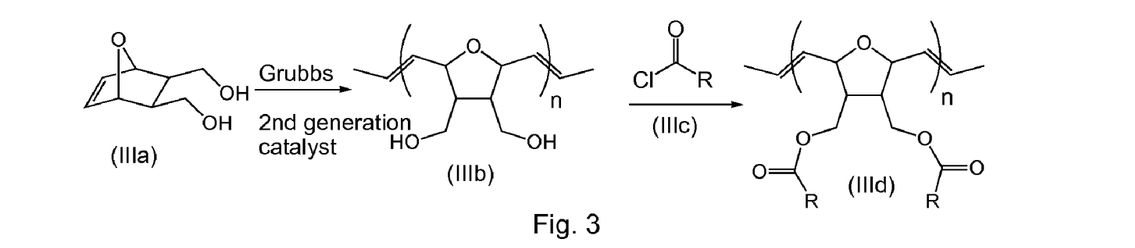
FIG. 3 is a schematic illustration of a method of forming polymers with hydrocarbon based groups, in accordance with an embodiment of the invention.

For instance, turning to FIG. 3, there is shown therein a process whereby a precursor monomer, for example, a hydroxyl or carboxyl norbornene derivative, specifically, 2,3-dihydroxymethyl,7-oxanorbornene (IIIa), is polymerized via a ROMP process to form a precursor polymer, specifically, poly(2,3-dihydroxymethyl,7-oxanorbornene) (IIIb). The precursor polymer (IIIb) is then chemically modified to provide the polymer with desired pendant groups (e.g., zwitterionic or hydrocarbon-based groups). For example, in FIG. 3, the hydroxyl groups of the precursor polymer are reacted with a suitable acid chloride, specifically R—CO—Cl (IIIc), where R is an organic radical which may be selected, for example, from —$(CH_2)_p$—$CH_3$, —$(CH_2)_m$—O—$(CH_2)_p$—$CH_3$, —$(CH_2)_m$—CO—O—$(CH_2)_p$—$CH_3$ or —$(CH_2)_m$—O—CO—$(CH_2)_p$—$CH_3$, where m is an integer between 0 and 5 and where p is an integer between 4 and 25. The result is a polymer (IIId) having hydrocarbon-based pendant groups, where n is an integer.

Figure 4:
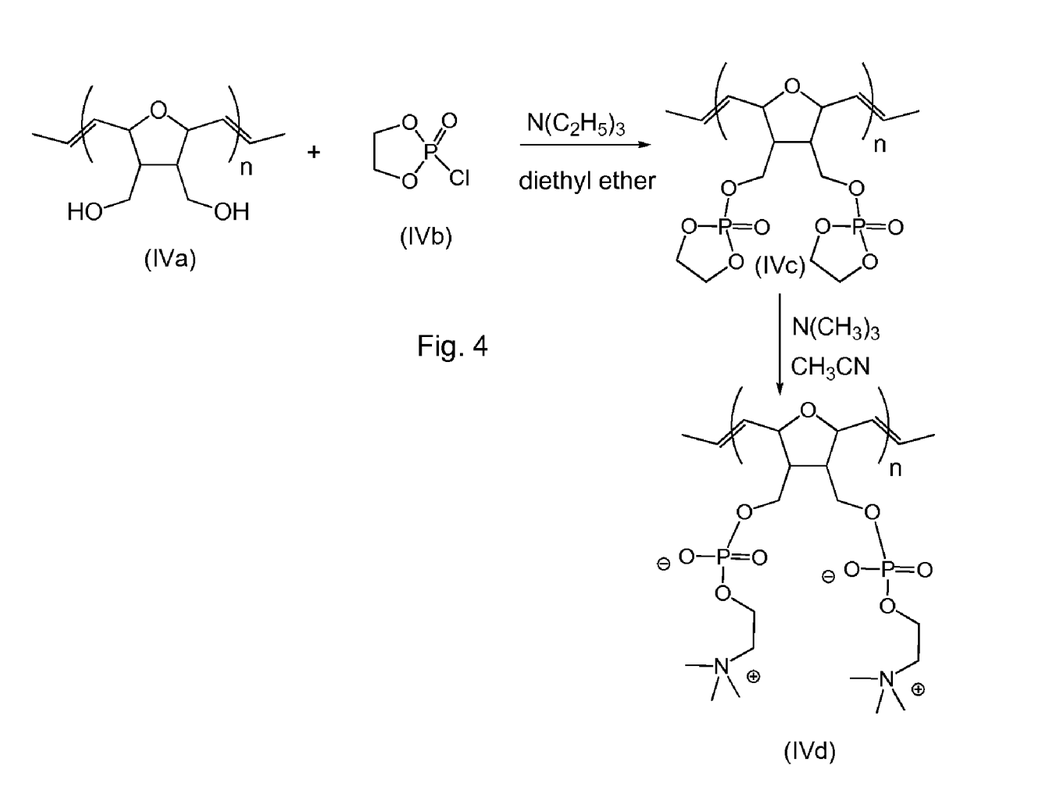
FIG. 4 is a schematic illustration of a method of forming polymers with zwitterionic groups, in accordance with an embodiment of the invention.

As another example, FIG. 4 illustrates a process whereby a precursor polymer, for example, a hydroxyl bearing precursor polymer, in particular, poly(2,3-dihydroxymethyl,7-oxanorbornene) (IVa), is reacted with 2-chloro-1,3,2-dioxaphospholane (IVb) in a solution containing triethylamine in diethyl ether to produce poly(2,3-diphosphorylmethyl-7-oxanorbornene) (IVc), which is reacted in a solution of trimethylamine in methyl cyanate to form the zwitterionic diphosphorylcholine norbornene polymer (IVd).

Copolymers comprising both hydrocarbon-based monomers and zwitterionic polymers can be formed using precursor polymers in various ways. For example, a first portion of the reactive groups of a precursor polymer (e.g., a first portion of the hydroxyl groups of a polymer like polymer (IIIb)/(IVa)) may be used for the attachment of hydrocarbon-based species (see, e.g., the process of FIG. 3), while a second portion of the reactive groups of the same precursor polymer (i.e., those remaining after the attachment of hydrocarbon-based species) may be used for the attachment of zwitterionic species (see, e.g., the process of FIG. 4), thereby forming a random copolymer.

In another specific example, a random copolymer may also be formed by copolymerizing a hydrocarbon-based monomer (see, e.g., compound (IIb), among many others) and a precursor monomer (see, e.g., compound (IIIa), among many others), followed by creation of zwitterionic species from the reactive groups on the incorporated precursor monomers, producing polymers with zwitterionic and hydrocarbon-based pendant groups.

Figure 5:
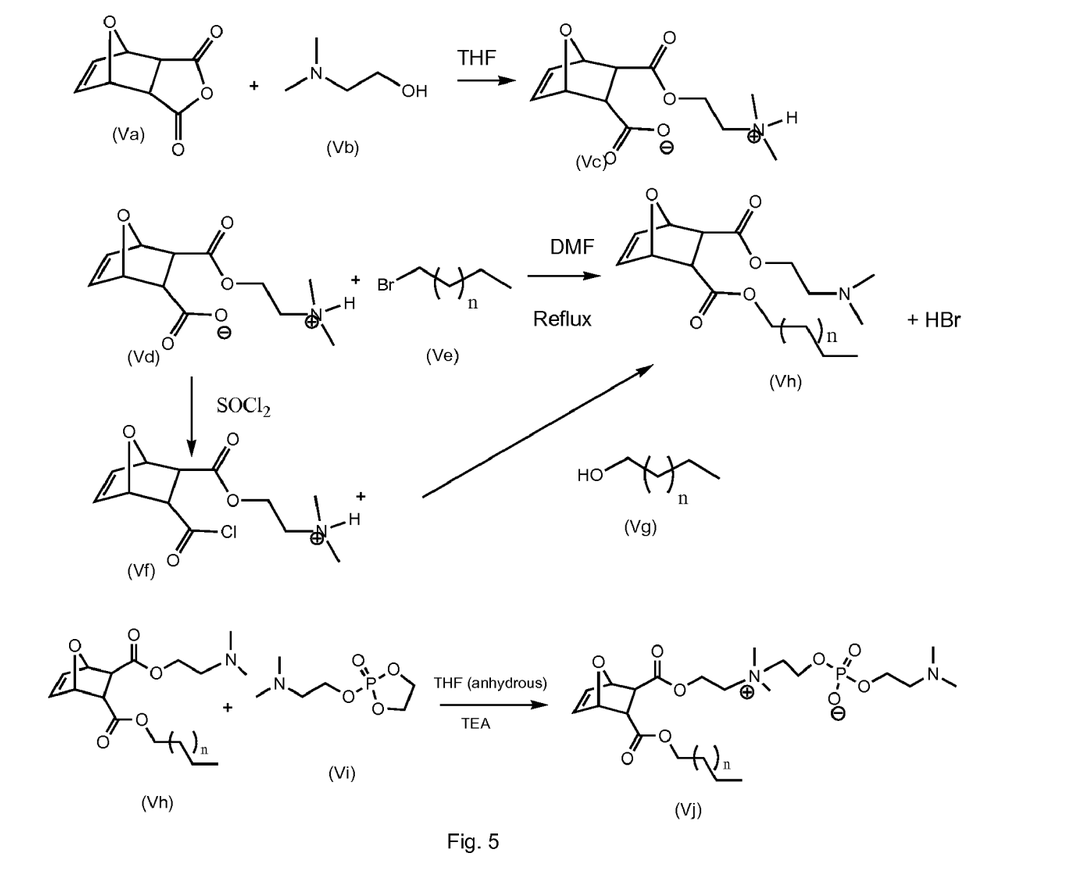
FIG. 5 is a schematic illustration of alternative method of forming monomers with hydrocarbon based groups and zwitterionic groups, in accordance with an embodiment of the invention.

In another embodiment of the invention shown in FIG. 5, a 7-oxanorbornene compound (Va) is reacted with an amino-alcohol (Vb) in THF to produce the zwitterionic oxanorbornene monomer (Vc). This monomer is then either (a) reacted with a bromo-terminated alkane (Ve) (where n ranges from 4 to 25), to produce a mixed monomer (Vh) (i.e., one having an amine group and a hydrocarbon group) or (b) reacted with thionyl chloride to form a zwitterionic acid chloride monomer (Vf) followed by reaction with a hydroxyl terminated alkane (Vg) (where n ranges from 4 to 25), to produce the mixed monomer Vh. The monomer Vh is then reacted with compound (Vi) in anyhydrous THF and triethylamine (TEA) to produce the mixed monomer (Vj) (i.e., having a zwitterionic phosphorylcholine group and a hydrocarbon group), which may be polymerized to form medical copolymers in accordance with the invention. See, e.g., S. Chen et al., *Langmuir* 2006, 22, 2418-2421.

Figure 6:
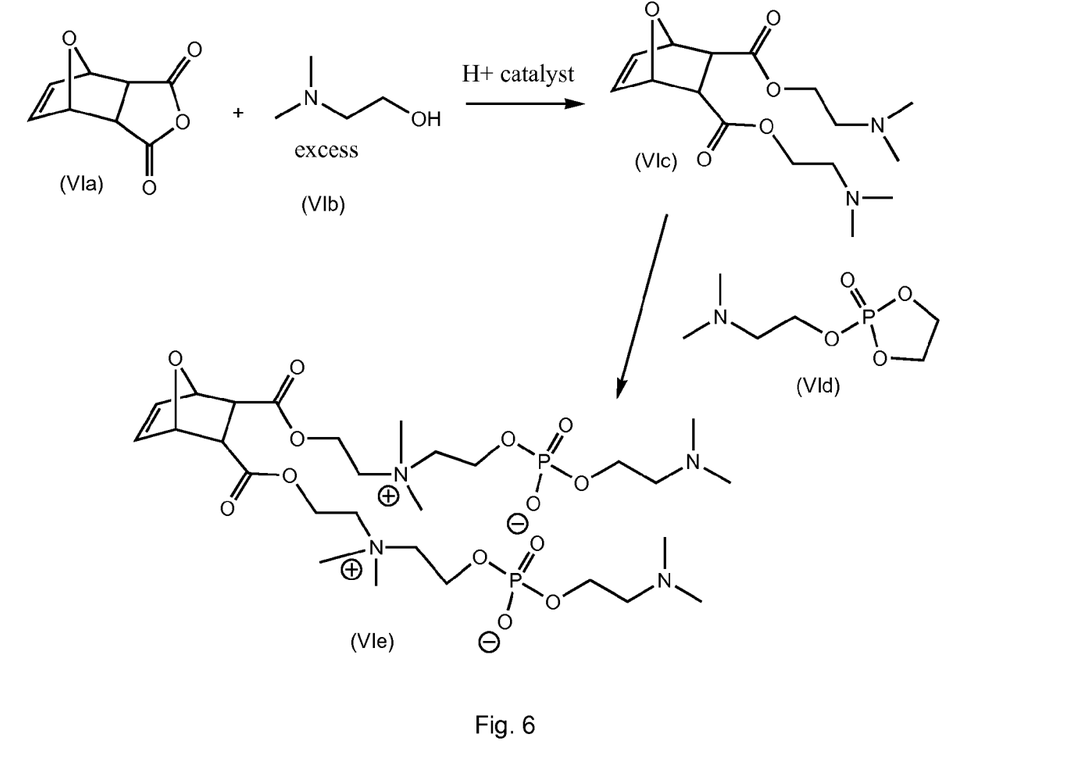
FIG. 6 is a schematic illustration of another method of forming monomers with zwitterionic groups, in accordance with an embodiment of the invention.

In yet another embodiment of the invention shown in FIG. 6, a 7-oxanorbornene compound (VIa) is reacted with excess amino-alcohol (VIb) in the presence of an acid catalyst to produce the oxanorbornene diamine compound (VIc). This monomer is then reacted with compound (VId), thereby forming the zwitterionic diphosphorylcholine oxanorbornene monomer, which may be polymerized to form medical copolymers in accordance with the invention. See, e.g., S. Chen et al., *Langmuir* 2006, 22, 2418-2421.

From the foregoing, it can be seen that the present invention provides design flexibility with respect to the type and distribution of the hydrocarbon-based groups and the zwitterionic groups, as well as their ratios to one another. This is desirable, for example, because these parameters will have an effect on a variety of copolymer properties.

In accordance with various aspects of the invention, medical products are provided that comprise the medical copolymers described above. Such medical products include, for example, pharmaceutical compositions (e.g., micellar compositions) and medical articles, including stents (including coronary vascular stents, peripheral vascular stents, cerebral, urethral, ureteral, biliary, tracheal, gastrointestinal and esophageal stents), stent coverings, stent grafts, vascular grafts, valves including heart valves and vascular valves, abdominal aortic aneurysm (AAA) devices (e.g., AAA stents, AAA grafts, etc.), vascular access ports, dialysis ports, embolization devices including cerebral aneurysm filler coils (including Guglielmi detachable coils and metal coils), embolic agents, tissue bulking devices, catheters (e.g., urological catheters or vascular catheters such as balloon catheters and various central venous catheters), guide wires, balloons, filters (e.g., vena cava filters and mesh filters for distil protection devices), septal defect closure devices, myocardial plugs, patches, ventricular assist devices including left ventricular assist hearts and pumps, total artificial hearts, shunts, implantable electrical stimulation systems such as spinal cord stimulation (SCS) systems, deep brain stimulation (DBS) systems, peripheral nerve stimulation (PNS) systems, cochlear implant systems, retinal implant systems, implantable pacemaker systems and implantable cardioverter-defibrillators (ICD's), tympanostomy tubes, thoracic drainage tubes, nephrostomy tubes, anastomosis clips and rings, and tissue engineering scaffolds for cartilage, bone, skin and other in vivo tissue regeneration, urethral slings, hernia "meshes", sutures, suture anchors, tissue staples and ligating clips at surgical sites, needles, cannulae, metal wire ligatures, introducers, artificial ligaments, tacks for ligament attachment and meniscal repair, joint prostheses, spinal discs and nuclei, orthopedic prosthesis such as bone grafts, bone plates, fins and fusion devices, orthopedic fixation devices such as interference screws in the ankle, knee, and hand areas, rods and pins for fracture fixation, screws and plates for craniomaxillofacial repair, dental implants, contact lenses, interocular lenses, punctum plugs, glaucoma shunts, wound dressings, biopsy devices, blood-contacting extracorporeal circuits including oxygenators and blood filters, as well as any medical article which is implanted or inserted into the body or which comes into contact with body fluids.

In various embodiments, medical articles are provided, which comprise polymeric regions that comprise the medical copolymers described above.

As used herein, a "polymeric region" is a region that contains polymers, for example, from 50 wt % or less to 75 wt % to 90 wt % to 95 wt % to 97.5 wt % to 99 wt % or more polymers.

In some embodiments, the polymeric regions of the present invention correspond to an entire medical article. In other embodiments, the polymeric regions correspond to one or more portions of a medical article. For instance, the polymeric regions can be in the form of medical article components, in the form of one or more fibers which are incorporated into a medical article, in the form of one or more polymeric layers formed over all or only a portion of an underlying substrate, and so forth. Materials for use as underlying medical article substrates include ceramic, metallic and polymeric substrates. As used herein a "layer" of a given material is a region of that material whose thickness is small (e.g., <25%) compared to both its length and width. As used herein a layer need not be planar, for example, taking on the contours of an underlying substrate. Layers can be discontinuous (e.g., patterned).

In addition to the above-described medical copolymers, the polymeric regions for use in the medical articles of the present invention may optionally further contain one or more of the following: (a) one or more therapeutic agents, (b) one or more supplemental polymers for blending with the medical copolymers of the invention (e.g., polystyrene, styrene-maleic anhydride copolymer, SIBS, PEG, etc.), and (c) one or more crosslinking agents.

Because the medical copolymers of the invention comprise carbon-carbon double bonds in their backbones in certain embodiments, they may be crosslinked using crosslinking agents such as di-norbornene type compounds, among others. Crosslinking agents may be employed, for example, to improve the in vivo stability of polymeric regions containing the copolymers of the invention or to modulate the rate of release of a therapeutic agent from such regions, if present.

"Therapeutic agents," "drugs," "pharmaceutically active agents," "pharmaceutically active materials," and other related terms may be used interchangeably herein.

Where the medical articles of the invention comprise polymeric regions that release therapeutic agents, the rate of release will depend, for example, on the nature of the therapeutic agent, the nature of the medical copolymer (e.g., molecular weight, architecture, and monomer composition, including hydrophilic/hydrophobic balance, etc.), and the nature any other optional supplemental species, including any supplemental crosslinking agent or any supplemental polymers within the polymeric regions.

A wide range of therapeutic agent loadings may be used in conjunction with the medical articles of the present invention. Typical loadings range, for example, from than 1 wt % or less to 2 wt % to 5 wt % to 10 wt % to 25 wt % or more of the polymeric region.

Exemplary therapeutic agents for use in conjunction with the present invention include the following: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promoters; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists.

Some examples of preferred therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Various techniques are available for forming polymeric regions in accordance with the present invention including solvent-based techniques. Using these techniques, a polymeric region can be formed, for instance, by (a) first providing a solution or dispersion that contains (i) polymer(s), including one or more medical copolymers in accordance with the invention and any supplemental polymer(s), (ii) any further optional supplemental agents such as therapeutic agent(s) and/or crosslinking agents, and (iii) a solvent, and (b) subsequently removing the solvent. The solvent that is ultimately selected will contain one or more solvent species, which are generally selected based on their ability to dissolve at least one of the polymer(s) that form the polymeric region, in addition to other factors, including drying rate, surface tension, etc. In certain embodiments, the solvent may be selected based on its ability to dissolve or disperse any supplemental agent(s) such as therapeutic agent(s) and/or crosslinking agents, if any. Where a crosslinking agent is provided, crosslinking may take place before, after, or concurrently with solvent removal. Preferred solvent-based techniques include, but are not limited to, solvent casting techniques, spin coating techniques, web coating techniques, solvent spraying techniques, dipping techniques, techniques employing an applicator (e.g., roller, brush, pen, etc.), techniques involving coating via mechanical suspension including air suspension, ink jet techniques, electrostatic techniques, fiber spinning techniques, and combinations of these processes.

Other processing techniques besides solvent-based processing techniques may also be used to form polymeric regions in accordance with the present invention. For example, where a polymeric region is formed from one or more polymers having thermoplastic characteristics, a variety of thermoplastic processing techniques may be used to form the polymeric region. Using these techniques, a polymeric region can be formed, for instance, by (a) first providing a melt that contains (i) polymer(s), for example, one or more medical copolymers in accordance with the invention and any supplemental polymer(s) (e.g., a thermoplastic polymer), and (ii) any further optional supplemental agents such as therapeutic agent(s) and/or crosslinking agents, and (b) subsequently cooling the melt. Where a crosslinking agent is provided, crosslinking may take place before, after, or concurrently with melt cooling. Examples of thermoplastic processing techniques, include compression molding, injection molding, blow molding, spraying, vacuum forming and calendaring, extrusion into sheets, fibers, rods, tubes and other cross-sectional profiles of various lengths, and combinations of these processes. Using these and other thermoplastic processing techniques, entire devices or portions thereof can be made.

In some embodiments of the invention, a polymer containing solution (where solvent-based processing is employed) or a polymer melt (where thermoplastic processing is employed) is applied to a substrate to form a polymeric region. For example, the substrate can correspond to all or a portion of a medical article to which a polymeric coating is applied, for example, by spraying, extrusion, and so forth. The substrate can also be, for example, a template, such as a mold, from which the polymeric region is removed after solidification. In other embodiments, for example, fiber-spinning, extrusion and co-extrusion techniques, one or more polymeric regions are formed without the aid of a substrate.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical product comprising a medical copolymer, said copolymer comprising (a) a polymer backbone that comprises (i) a plurality of —C=C— groups within the polymer backbone, (ii) a plurality of —$R_9$— groups within the polymer backbone, wherein $R_9$ comprises a radical-substituted C2-C10 cyclic or heterocyclic group, or (iii) both a plurality of —C=C— groups within the polymer backbone and a plurality of —$R_9$— groups within the polymer backbone, (b) a plurality of hydrocarbon-based pendant groups along the polymer backbone that comprise a saturated or unsaturated carbon chain of at least four carbons in length, and (c) a plurality of zwitterionic pendant groups along the polymer backbone that comprise a positively charged quaternary ammonium group and a negatively charged phosphate group, wherein the copolymer comprises a plurality of monomers selected from wherein $R^1$ and $R^2$ are selected from —H, —$(CH_2)_m$—OH, —$(CH_2)_m$—COOH, —$(CH_2)_p$—$CH_3$, —$(CH_2)_m$—O—$(CH_2)_p$—$CH_3$, —$(CH_2)_m$—CO—O—$(CH_2)_p$—$CH_3$, —$(CH_2)_m$—O—CO—$(CH_2)_p$—$CH_3$, wherein m is an integer between 0 and 5, wherein p is an integer between 4 and 25, and wherein at least one of $R^1$ and $R^2$ is not —H, —$(CH_2)_m$—OH or —$(CH_2)_m$—COOH.

2. The medical product of claim 1, wherein $R_9$ comprises said heterocyclic group.

3. The medical product of claim 1, wherein the copolymer comprises a plurality of hydrocarbon-based pendant groups selected from —$(CH_2)_p$—$CH_3$, —$(CH_2)_m$—O—$(CH_2)_p$—$CH_3$, —$(CH_2)_m$—CO—O—$(CH_2)_p$—$CH_3$ and —$(CH_2)_m$—O—CO—$(CH_2)_p$—$CH_3$, where m is an integer between 0 and 5 and p is an integer between 4 and 25.

4. The medical product of claim 1, wherein the zwitterionic pendant groups are selected from groups and groups, where k is an integer between 0 and 5 and m is an integer between 0 and 5.

5. The medical product of claim 1, wherein said hydrocarbon-based pendant groups and said zwitterionic pendant groups are randomly distributed within said copolymer.

6. The medical product of claim 1, wherein the copolymer is a block copolymer comprising (a) a first polymer block comprising a first polymer backbone that comprises a plurality of said —C=C— groups, a plurality of said —$R_9$— groups, or both, and a plurality of said hydrocarbon-based pendant groups along said first polymer backbone and (b) a second polymer block comprising a second polymer backbone that comprises a plurality of said —C=C— groups, a plurality of said —$R_9$— groups, or both, and a plurality of said zwitterionic pendant groups along said second polymer backbone.

7. The medical product of claim 6, wherein said block copolymer is an amphiphilic block copolymer.

8. The medical product of claim 7, wherein said medical product comprises a micelle that comprises said amphiphilic block copolymer.

9. The medical product of claim 1, wherein said copolymer is formed by a ring-opening metathesis polymerization process.

10. The medical product of claim 1, wherein said medical product is a medical article comprising a polymeric region that comprises said copolymer.

11. The medical article of claim 10, wherein said polymeric region comprises ruthenium.

12. The medical article of claim 10, wherein said polymeric region corresponds to an entire medical article, to a component of a medical article, or to a layer that at least partially covers an underlying substrate.

13. The medical article of claim 10, wherein said polymeric region further comprises a therapeutic agent.

14. The medical article of claim 10, wherein said polymeric region further comprises a crosslinking agent.

15. The medical article of claim 10, wherein said polymeric region further comprises an additional polymer.

16. The medical article of claim 10, wherein said medical article is an implantable or insertable medical device.

17. The medical article of claim 16, wherein said medical device is a stent.

* * * * *